(12) United States Patent
Gyakushi et al.

(10) Patent No.: US 10,299,897 B2
(45) Date of Patent: May 28, 2019

(54) DENTAL PLATE LINER

(71) Applicant: TOKUYAMA DENTAL CORPORATION, Taito-ku, Tokyo (JP)

(72) Inventors: Ayumu Gyakushi, Tokyo (JP); Kouji Matsushige, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 0 days.

(21) Appl. No.: 15/107,288

(22) PCT Filed: Jan. 6, 2015

(86) PCT No.: PCT/JP2015/050166
§ 371 (c)(1),
(2) Date: Jun. 22, 2016

(87) PCT Pub. No.: WO2015/105103
PCT Pub. Date: Jul. 16, 2015

(65) Prior Publication Data
US 2017/0007378 A1    Jan. 12, 2017

(30) Foreign Application Priority Data

Jan. 10, 2014  (JP) ................................ 2014-003381

(51) Int. Cl.
*A61K 6/00* (2006.01)
*A61C 13/07* (2006.01)

(52) U.S. Cl.
CPC ........ *A61C 13/0025* (2013.01); *A61K 6/0026* (2013.01)

(58) Field of Classification Search
CPC .................................................. A61K 6/0026
See application file for complete search history.

(56) References Cited

U.S. PATENT DOCUMENTS

| 6,410,612 B1 * | 6/2002 | Hatanaka ............. A61K 6/0026 433/228.1 |
| 2002/0061937 A1 | 5/2002 | Kobayashi et al. |
| 2012/0196952 A1 * | 8/2012 | Suzuki ................ A61K 6/0023 523/116 |

FOREIGN PATENT DOCUMENTS

| JP | 1992042364 B | 7/1992 |
| JP | 2000175941 A | 6/2000 |
| JP | 2000254152 A | 9/2000 |
| JP | 2000312689 A | 11/2000 |
| JP | 2002097109 A | 4/2002 |
| JP | 2005255654 A | 9/2005 |
| JP | 2006111584 A | 4/2006 |
| JP | 3967488 B2 | 8/2007 |
| JP | 4255596 B2 | 4/2009 |
| JP | 4698806 B2 | 6/2011 |

OTHER PUBLICATIONS

International Search Report corresponding to Application No. PCT/JP2015/050166; dated Mar. 24, 2015, with English translation.

* cited by examiner

*Primary Examiner* — Michael F Pepitone
(74) *Attorney, Agent, or Firm* — Cantor Colburn LLP

(57) ABSTRACT

The dental plate liner includes: a paste (i) containing (A) a (meth)acrylic acid-based polymer, and a fluorine-containing (meth)acrylic acid-based polymerizable monomer in which (A) the (meth)acrylic acid-based polymer has a solubility of less than 20 mass %; and a paste (ii) containing a (meth) acrylic acid-based polymerizable monomer in which (A) the (meth)acrylic acid-based polymer has a solubility of 20 mass % or more, and a filler, in which at least one paste selected from the group consisting of the paste (i) and the paste (ii) contains a polymerization initiator, and in which the dental plate liner is used through mixing of the paste (i) and the paste (ii) immediately before use.

7 Claims, No Drawings

016
DENTAL PLATE LINER

CROSS REFERENCE TO RELATED APPLICATIONS

This is the U.S. national stage of application No. PCT/JP2015/050166, filed on Jan. 6, 2015. Priority under 35 U.S.C. § 119(a) and 35 U.S.C. § 365(b) is claimed from Japanese Application No. 2014-003381, filed Jan. 10, 2014, the disclosure of which is also incorporated herein by reference.

TECHNICAL FIELD

The present invention relates to a dental plate liner.

BACKGROUND ART

A dental plate liner is a material for rebasing a denture, which has become unfitted for the oral mucosa of a patient through long-term use, and is used to repair the denture to a usable state again. As a curable material to be used for such material, there is widely used a radically polymerizable curable material formed of a monomer capable of being polymerized in the presence of a radical, and a radical polymerization initiator.

Such material is used by being cured through heating outside the mouth or directly cured in the mouth, and is often used by the latter technique, i.e., a so-called direct method, which involves inserting the material directly into the mouth of the patient, fitting the material to an oral mucosal surface, and then polymerizing and curing the material held in the mouth to perform the repair.

Hitherto, as such liner, there has been generally used a curable material including: a liquid material containing, as a main component, a polymerizable monomer, such as methyl methacrylate; and a powder material containing, as a main component, a (meth)acrylic acid-based polymer, such as polymethyl methacrylate, polyethyl methacrylate, or a copolymer of methyl methacrylate and ethyl methacrylate, and having added thereto a radical polymerization initiator typified by an organic peroxide or the like (for example, Patent Literatures 1 and 2).

As an advantage of such dental plate liner to be used through mixing of the powder material and the liquid material before use, there is given a unique time-dependent change in viscosity thereof. That is, in such dental plate liner, when the powder material and the liquid material are mixed, the (meth)acrylic acid-based polymer gradually dissolves in and swells with the polymerizable monomer. Accordingly, fluidity is high immediately after the mixing because the amount of the polymer component dissolving in and swelling with the polymerizable monomer component is small, but the dissolution and swelling proceed to increase the viscosity along with permeation of the monomer component into the polymer component. Then, after undergoing a dough state which allows plastic deformation, the mixture is brought into a dough state which does not allow plastic deformation. Simultaneously, such dental plate liner has the following function: the radical polymerization initiator is mixed in the liner to generate a radical, and after a lapse of a predetermined period of time from the mixing, polymerization and curing proceed.

Meanwhile, the rebase of a denture by the direct method is performed through: 1) an operation of arranging the dental plate liner on the dental plate mucosal surface; 2) an operation of inserting the dental plate liner into the mouth, followed by molding; and 3) an operation of removing and adjusting the dental plate liner. In this case, at the time of 2) the molding operation, when an attempt is made to mold the dental plate liner under a non-dough state having a low viscosity, a sufficient thickness cannot be secured. In contrast, when the viscosity is excessively increased, an accurate impression cannot be taken. In addition, when there is a risk in that the dental plate liner may become unremovable when directly cured owing to, for example, the presence of an undercut, 3) the dental plate liner is temporarily removed and adjusted before the curing in some cases. In those cases, the dental plate liner is removed from the mouth after being brought into a dough state which does not allow plastic deformation even by removal with a higher viscosity than that at the time of the molding.

The dental plate liner to be used through mixing of the powder material and the liquid material can facilitate clinical or technical work through good use of time-dependent changes in paste properties by performing: 1) the arranging operation during the high-fluidity period immediately after the mixing; 2) the molding operation under the subsequent dough state which allows plastic deformation; and 3) the adjusting operation under the dough state which does not allow plastic deformation.

However, the dental plate liner to be used through mixing of the powder material and the liquid material requires operations for measuring and mixing immediately before use, and complexity of the work poses a significant drawback in some cases.

For example, in contemporary Japan, which is undergoing a further transition from an aging society to a super-aging society, there is a tendency in the field of dentistry that the number of cases of office visit treatment reduces and the number of cases of home (visit) treatment increases. In such home treatment, the procedure involving measuring the amounts of the powder material and the liquid material immediately before use as described above has hygienic trouble due to dust of powder or the like and trouble due to air bubble incorporation during kneading or the like, and has a risk of giving an unpleasant feeling to an operator or a patient because of the odor and irritating property of the monomer due to high volatility of the monomer in the mixture.

Under such circumstances, as related art for alleviating the complexity of the measuring and mixing of the powder material and the liquid material, and the unpleasant feeling to be given to the operator or the patient, there are disclosures of a dental plate liner which uses no powder material. That is, there are proposals of: a paste-like resin material for a dental plate formed of a polymerizable monomer, a (meth)acrylate-based polymer, and a thermal polymerization catalyst and/or a photopolymerization catalyst (Patent Literature 3); a paste-like or clay-like repair material composition for a dental plate formed of a first component and a second component (Patent Literature 4); and a resin composition for a dental plate formed of a liquid A including a high molecular weight polymer of a (meth)acrylate or the like, a monomer, and a polymerization initiator, and a liquid B including a high molecular weight polymer of a (meth)acrylate or the like, and a monomer (Patent Literature 5).

Meanwhile, it has been pointed out that the related-art dental plate liner also has a hygienic problem of being extremely liable to be stained because, when used in the mouth, the dental plate liner is liable to, for example, be colored, have an odor, and absorb water over time. In order to alleviate such stain, there is also a proposal of a dental plate liner characterized by using a fluorine-containing (meth)acrylate and a polyfunctional (meth)acrylate (Patent Literature 6).

CITATION LIST

Patent Literature

[PTL 1] JP 3967488 B2
[PTL 2] JP 04-042364 B2
[PTL 3] JP 2000-254152 A
[PTL 4] JP 2000-175941 A
[PTL 5] JP 4698806 B2
[PTL 6] JP 4255596 B2

SUMMARY OF INVENTION

Technical Problem

However, the resin composition for a dental plate formed of the liquid, paste-like, or clay-like composition disclosed in each of Patent Literatures 3 to 5, though being able to alleviate the problems such as the complexity of measuring and mixing and the unpleasant feeling given to the operator or the patient, has a drawback of not having time-dependent changes in paste properties suitable for clinical or technical work.

That is, the dental plate liner of Patent Literature 3 is a single paste in which a polymer component has already dissolved in a monomer component, and hence a change in viscosity does not occur. In addition, the dental plate liner of Patent Literature 4, though being a composition formed of a first component and a second component, does not contain a polymer component soluble in a monomer component. Accordingly, also in this case, a viscosity change caused by the dissolution/swelling of the polymer component in/with the monomer component at the time of mixing does not occur. In addition, in Patent Literature 5, a polymer component soluble in a monomer component is contained, and hence a viscosity change occurs at the time of mixing. However, an investigation made by the inventors of the present invention has found that the viscosity change is not a time-dependent viscosity change suitable for clinical or technical work.

In addition, as described above, the dental plate liner of such a type that a powder material and a liquid material are mixed immediately before use has an advantage of having a time-dependent viscosity change suitable for clinical or technical work, but has the problems such as the complexity of operations and the unpleasant feeling given to the operator or the patient.

Meanwhile, the dental plate liner using no powder material, which does not have the problems such as the complexity of operations and the unpleasant feeling given to the operator or the patient, does not have a time-dependent viscosity change suitable for clinical or technical work.

In view of the foregoing, there has been a demand for a dental plate liner which has a paste-like form, and has a time-dependent viscosity change optimum for clinical or technical work at the time of mixing.

In addition, when the dental plate liner has a paste-like form, the complexity of workability is alleviated and the risk of air bubble incorporation at the time of kneading is alleviated, but the hygienic problem of, for example, being liable to be stained due to coloring or the like over time remains.

The dental plate liner characterized by using a fluorine-containing (meth)acrylate and a polyfunctional (meth)acrylate, which is disclosed in Patent Literature 6, alleviates the problem of the stain due to coloring or the like over time, but has a problem in clinical or technical work. Therefore, there has been a strong demand for the development of a dental plate liner which has a paste-like form, has an optimum viscosity increase effect at the time of mixing, and is less liable to be stained due to coloring over time.

Solution to Problem

The inventors of the present invention have made extensive investigations in order to solve the above-mentioned problems, and as a result, have found that, when a first paste containing a (meth)acrylic acid-based polymer and a fluorine-containing (meth)acrylic acid-based polymerizable monomer which hardly dissolves the (meth)acrylic acid-based polymer, and a second paste containing a (meth)acrylic acid-based polymerizable monomer which easily dissolves the (meth)acrylic acid-based polymer are used in combination, despite a paste type, a viscosity increase peculiar to a powder material/liquid material type is obtained, and a stain due to coloring over time can be suppressed. Thus, the inventors have completed the present invention.

That is, according to one embodiment of the present invention, there is provided a dental plate liner, including:
a paste (i) containing
(A) a (meth)acrylic acid-based polymer, and
(B) a fluorine-containing (meth)acrylic acid-based polymerizable monomer in which (A) the (meth)acrylic acid-based polymer has a solubility of less than 20 mass %; and
a paste (ii) containing
(C) a (meth)acrylic acid-based polymerizable monomer in which (A) the (meth)acrylic acid-based polymer has a solubility of 20 mass % or more, and
(D) a filler,
in which at least one paste selected from the group consisting of the paste (i) and the paste (ii) contains (E) a polymerization initiator, and
in which the dental plate liner is used through mixing of the paste (i) and the paste (ii) immediately before use.

Advantageous Effects of Invention

The dental plate liner of the present invention is a material excellent in workability which has a paste-like form free of the complexity of the measuring and mixing of a powder material and a liquid material, and in which, at the time of mixing, (A) the (meth)acrylic acid-based polymer, which is contained in the paste (i), dissolves in and swells with (C) the (meth)acrylic acid-based polymerizable monomer in which (A) the (meth)acrylic acid-based polymer has a solubility of 20 mass % or more, the monomer being contained in the paste (ii), and thus a time-dependent viscosity increase comparable to that of a related-art dental plate liner formed of a powder material and a liquid material can be obtained.

Further, by virtue of the use of (B) the fluorine-containing (meth)acrylic acid-based polymerizable monomer in which (A) the (meth)acrylic acid-based polymer has a solubility of less than 20 mass %, coloring or the like of a cured product after curing is alleviated to be less liable to cause a stain. Moreover, during the storage of the paste (i), (A) the (meth)acrylic acid-based polymer does not gradually swell with (B) the fluorine-containing (meth)acrylic acid-based polymerizable monomer in which (A) the (meth)acrylic acid-based polymer has a solubility of less than 20 mass %, and hence the change in viscosity of the paste (i) can remain a slight time-dependent one, to thereby allow use over a long period of time.

DESCRIPTION OF EMBODIMENTS

A dental plate liner according to one embodiment of the present invention includes: a paste (i) containing (A) a (meth)acrylic acid-based polymer, and (B) a fluorine-containing (meth)acrylic acid-based polymerizable monomer in which (A) the (meth)acrylic acid-based polymer has a solubility of less than 20 mass % (hereinafter sometimes abbreviated as "(B) the fluorine-containing (meth)acrylic acid-based polymerizable monomer"); and a paste (ii) containing (C) a (meth)acrylic acid-based polymerizable monomer in which (A) the (meth)acrylic acid-based polymer has a solubility of 20 mass % or more (hereinafter sometimes abbreviated as "(C) the (meth)acrylic acid-based polymerizable monomer"), and (D) a filler, in which at least one paste selected from the group consisting of the paste (i) and the paste (ii) contains (E) a polymerization initiator, and in which the dental plate liner is used through mixing of the paste (i) and the paste (ii) immediately before use. It is generally preferred that the dental plate liner according to this embodiment consist of the paste (i) and the paste (ii).

Herein, in particular, the greatest feature of the dental plate liner according to this embodiment lies in combined use of two kinds of (meth)acrylic acid-based polymerizable monomers different from each other in dissolution property of (A) the (meth)acrylic acid-based polymer, that is, (B) the fluorine-containing (meth)acrylic acid-based polymerizable monomer and (C) the (meth)acrylic acid-based polymerizable monomer. With this, in the dental plate liner according to this embodiment, at the time of the mixing of the paste (i) and the paste (ii), (A) the (meth)acrylic acid-based polymer, which is contained in the paste (i), dissolves in and swells with (C) the (meth)acrylic acid-based polymerizable monomer in which (A) the (meth)acrylic acid-based polymer has a solubility of 20 mass % or more, the monomer being contained in the paste (ii), and thus a viscosity increase comparable to that of a related-art dental plate liner formed of a powder material and a liquid material can be obtained. When a (meth)acrylic acid-based polymerizable monomer in which (A) the (meth)acrylic acid-based polymer has a solubility of less than 20 mass % is used as the component (C), the dissolution and swelling speed of (A) the (meth) acrylic acid-based polymer at the time of the mixing of the paste (i) and the paste (ii) is slowed. Accordingly, the viscosity increase comparable to that of the related-art dental plate liner formed of a powder material and a liquid material cannot be obtained.

In addition, by virtue of the use of (B) the fluorine-containing (meth)acrylic acid-based polymerizable monomer in which (A) the (meth)acrylic acid-based polymer has a solubility of less than 20 mass %, coloring or the like is alleviated to be less liable to cause a stain, and a time-dependent change in viscosity of the paste due to gradual swelling of (A) the (meth)acrylic acid-based polymer during storage is suppressed. When a fluorine-containing (meth)acrylic acid-based polymerizable monomer in which (A) the (meth)acrylic acid-based polymer has a solubility of 20 mass % or more is used as the component (B), (A) the (meth) acrylic acid-based polymer dissolves and swells to cause a remarkable time-dependent change in viscosity of the paste during the storage of the paste (i), resulting in difficulty in use.

In addition, by virtue of the use of (B) the fluorine-containing (meth)acrylic acid-based polymerizable monomer in which (A) the (meth)acrylic acid-based polymer has a solubility of less than 20 mass %, coloring or the like of a cured product after curing is alleviated to be less liable to cause a stain. Moreover, during the storage of the paste (i), (A) the (meth)acrylic acid-based polymer does not gradually swell with (B) the fluorine-containing (meth)acrylic acid-based polymerizable monomer in which (A) the (meth) acrylic acid-based polymer has a solubility of less than 20 mass %, and hence the change in viscosity of the paste (i) can remain a slight time-dependent one, to thereby allow use over a long period of time. In addition, also in the paste (ii), its main components are (C) the (meth)acrylic acid-based polymerizable monomer in which (A) the (meth)acrylic acid-based polymer has a solubility of 20 mass % or more, and (D) the filler which does not dissolve in this polymerizable monomer, and hence a time-dependent change in viscosity of the paste (ii) cannot substantially occur. Accordingly, the dental plate liner according to this embodiment as a whole is also excellent in storability.

The solubility means the upper limit value of a concentration at which (A) the (meth)acrylic acid-based polymer can dissolve in a polymerizable monomer. In the description of the present application, the solubility was simply determined by visually evaluating a concentration at which (A) the (meth)acrylic acid-based polymer dissolved in the polymerizable monomer at 23° C. when (A) the (meth) acrylic acid-based polymer was added at a content within the range of from 5 mass % to 50 mass % to the polymerizable monomer. In the description of the present application: the solubility was defined as less than 5 mass % when 5 mass % of (A) the (meth)acrylic acid-based polymer did not dissolve; the concentration at which (A) the (meth)acrylic acid-based polymer actually dissolved was defined as the solubility when (A) the (meth)acrylic acid-based polymer dissolved at a concentration within the range of 5 mass % or more and less than 50 mass %; and the solubility was defined as 50 mass % or more when all of 50 mass % of (A) the (meth)acrylic acid-based polymer dissolved.

In the dental plate liner according to this embodiment, as (A) the (meth)acrylic acid-based polymer, a known polymer which may be generally used in a dental material may be used as long as the polymer satisfies the requirements of having a solubility of less than 20 mass % in (B) the fluorine-containing (meth)acrylic acid-based polymerizable monomer, and having a solubility of 20 mass % or more in (C) the (meth)acrylic acid-based polymerizable monomer. In the description of the present application, the term "(A) the (meth)acrylic acid-based polymer" more exactly means a non-cross-linked (meth)acrylic acid-based polymer, and excludes a cross-linked (meth)acrylic acid-based polymer which is hardly compatible with (C) the (meth)acrylic acid-based polymerizable monomer. Specific examples of (A) the (meth)acrylic acid-based polymer include: a homopolymer of methyl (meth)acrylate, ethyl (meth)acrylate, t-butyl (meth)acrylate, n-butyl (meth)acrylate, lauryl (meth)acrylate, dodecyl (meth)acrylate, stearyl (meth)acrylate, cyclohexyl (meth)acrylate, benzyl (meth)acrylate, isobornyl (meth)acrylate, isopropyl (meth)acrylate, 2-hydroxyethyl (meth)acrylate, 3-hydroxypropyl (meth)acrylate, isobutyl (meth)acrylate, butoxyethyl (meth)acrylate, hydroxypropyl (meth)acrylate, tetrahydrofurfuryl (meth)acrylate, glycidyl (meth)acrylate, 2-methoxyethyl (meth)

acrylate, 2-ethylhexyl (meth)acrylate, or benzyl (meth)acrylate and a copolymer thereof; and a copolymer of a (meth) acrylic acid-based monomer and any other polymerizable monomer, such as poly(styrene-ethyl methacrylate). One kind of those polymers may be used alone, or two or more kinds thereof may be used in combination.

The average molecular weight of (A) the (meth)acrylic acid-based polymer is not particularly limited. However, when the average molecular weight is 1,000,000 or more, the speed of dissolution is slowed, and a moderate viscosity increase at the time of the mixing of the pastes is not obtained, and when the average molecular weight is 50,000 or less, there is a risk in that a moderate viscosity may not be obtained even after dissolution. From the viewpoints of, in addition to the foregoing, the mechanical strength and other physical properties of the cured product to be obtained, the average molecular weight is preferably from 50,000 to 1,000,000, more preferably from 100,000 to 700,000. In the description of the present application, the "average molecular weight" means a weight-average molecular weight.

As (A) the (meth)acrylic acid-based polymer, a solid (generally particulate) (meth)acrylic acid-based polymer is used. The particle diameter of the (meth)acrylic acid-based polymer is not particularly limited. However, when the particle diameter is excessively large, the viscosity increase is slowed, and in contrast, when the particle diameter is excessively small, the viscosity increase is excessively accelerated. In order to obtain a moderate viscosity increase at the time of the mixing of the pastes, the particle diameter is preferably from 1 μm to 100 μm, more preferably from 5 μm to 80 μm.

The blending ratio ((A)/(C)) of (A) the (meth)acrylic acid-based polymer to (C) the (meth)acrylic acid-based polymerizable monomer in which (A) the (meth)acrylic acid-based polymer has a solubility of 20 mass % or more is preferably from 0.9 to 3.0, more preferably from 1.2 to 2.5, most preferably from 1.4 to 2.0. When the blending ratio ((A)/(C)) is set to fall within the range of from 0.9 to 3.0, in the dissolution of (A) the (meth)acrylic acid-based polymer at the time of the mixing of the paste (i) and the paste (ii), the dissolution speed of (A) the (meth)acrylic acid-based polymer can be easily made more moderate within such a range as not to be excessively small and not to be excessively large. Consequently, properties suitable for a state in which the mixture of the paste (i) and the paste (ii) can be molded in the mouth and then removed and trimmed are more easily obtained for a sufficient period of time, and a period of time for the mixture to be inserted into the mouth and molded is also more easily secured sufficiently.

As (B) the fluorine-containing (meth)acrylic acid-based polymerizable monomer in which (A) the (meth)acrylic acid-based polymer has a solubility of less than 20 mass %, a fluorine-containing (meth)acrylic acid-based polymerizable monomer represented by the following formula (I) is more suitably used.

$$CH_2=CR^1COOR^2-Rf \qquad (I)$$

(In the formula (I), $R^1$ represents a hydrogen atom or a methyl group, $R^2$ represents an alkyl group having 1 to 20 carbon atoms, and Rf represents a fluoroalkyl group having 1 to 20 carbon atoms.)

Specific examples of the fluorine-containing (meth) acrylic acid-based polymerizable monomer represented by the formula (I) include perfluorooctylethyl (meth)acrylate, 2-(perfluorobutyl)ethyl (meth)acrylate, 2-(perfluorohexyl) ethyl (meth)acrylate, and 1H,1H,3H-hexafluorobutyl (meth) acrylate.

In order to prevent the generation of a change in viscosity of the paste (i) due to the dissolution of (A) the (meth)acrylic acid-based polymer during storage before the mixing of the paste (i) and the paste (ii), the solubility of (A) the (meth) acrylic acid-based polymer needs to be less than 20 mass %, more preferably less than 5 mass %. In addition, (B) the fluorine-containing (meth)acrylic acid-based polymerizable monomer may be a combination of two or more kinds of monomers. When (B) the fluorine-containing (meth)acrylic acid-based polymerizable monomer is a combination of two or more kinds of monomers, the solubility of (A) the (meth)acrylic acid-based polymer only needs to be less than 20 mass % in (B) the mixture of two or more kinds of fluorine-containing (meth)acrylic acid-based polymerizable monomers, and the monomers constituting the mixture may include a monomer in which (A) the (meth)acrylic acid-based polymer has a solubility of 20 mass % or more.

An excessively large blending amount of (B) the fluorine-containing (meth)acrylic acid-based polymerizable monomer in which (A) the (meth)acrylic acid-based polymer has a solubility of less than 20 mass % causes an odor and an irritating property, and an excessively small blending amount thereof makes the paste difficult to handle. Therefore, the blending amount in the paste (i) is preferably from 20 parts by mass to 70 parts by mass, more preferably from 30 parts by mass to 50 parts by mass with respect to 100 parts by mass of the total amount of (A) the (meth)acrylic acid-based polymer and (B) the fluorine-containing (meth) acrylic acid-based polymerizable monomer in which (A) the (meth)acrylic acid-based polymer has a solubility of less than 20 mass %.

As (C) the (meth)acrylic acid-based polymerizable monomer in which (A) the (meth)acrylic acid-based polymer has a solubility of 20 mass % or more, A known one which may be generally used in a dental material may be used as long as the requirement that the solubility of (A) the (meth) acrylic acid-based polymer therein be 20 mass % or more is satisfied. Specific examples thereof include: monofunctional (meth)acrylic acid-based polymerizable monomers, such as methyl (meth)acrylate, ethyl (meth)acrylate, isopropyl (meth)acrylate, hydroxyethyl (meth)acrylate, tetrahydrofurfuryl (meth)acrylate, and glycidyl (meth)acrylate; 2,2-bis (methacryloyloxyphenyl)propane, 2,2-bis[4-(3-methacryloyloxy)-2-hydroxypropoxyphenyl]propane, 2,2-bis(4-methacryloyloxyphenyl)propane, 2,2-bis(4-methacryloyloxypolyethoxyphenyl)propane, and 2,2-bis(4-methacryloyloxydiethoxyphenyl)propane), and an acrylate corresponding to each of those methacrylates; bifunctional (meth)acrylic acid-based polymerizable monomers, such as 2-hydroxyethyl (meth)acrylate, 2-hydroxypropyl (meth) acrylate, 3-chloro-2-hydroxypropyl (meth)acrylate, ethylene glycol di(meth)acrylate, diethylene glycol di(meth)acrylate, triethylene glycol di(meth)acrylate, butylene glycol di(meth)acrylate, neopentyl glycol di(meth)acrylate, propylene glycol di(meth)acrylate, 1,3-butanediol di(meth)acrylate, 1,4-butanediol di(meth)acrylate, 1,6-hexanediol di(meth) acrylate, 1,9-nonanediol di(meth)acrylate, 2-hydroxyethyl (meth)acrylate, 2-hydroxypropyl (meth)acrylate, and 3-chloro-2-hydroxypropyl (meth)acrylate; and trifunctional (meth)acrylic acid-based polymerizable monomers, such as trimethylolpropane tri(meth)acrylate, trimethylolethane tri (meth)acrylate, pentaerythritol tri(meth)acrylate, and trimethylolmethane tri(meth)acrylate.

Those (meth)acrylic acid-based polymerizable monomers may each be used alone, or two or more kinds thereof may be used in combination. In particular, the case where a monofunctional polymerizable monomer and a bifunctional or tri- or higher functional polymerizable monomer are used in combination is preferred because the mechanical properties, such as strength and durability, of the cured body to be obtained can be made satisfactory by blending the bifunctional or tri- or higher functional polymerizable monomer in a large amount. In addition, when two or more kinds of polymerizable monomers are used in combination, the solubility of (A) the (meth)acrylic acid-based polymer only needs to be 20 mass % or more in (C) the mixture of two or more kinds of monomers, and as long as this requirement is satisfied, the monomers constituting the mixture may include a monomer in which (A) the (meth)acrylic acid-based polymer has a solubility of less than 20 mass %.

In particular, in order to obtain a rapid viscosity increase when mixing the paste (i) and the paste (ii), a (meth)acrylic acid-based polymerizable monomer in which (A) the (meth) acrylic acid-based polymer has a solubility of 50 mass % or more is preferred.

An excessively large blending amount of (C) the (meth) acrylic acid-based polymerizable monomer in which (A) the (meth)acrylic acid-based polymer has a solubility of 20 mass % or more causes an odor and an irritating property, and an excessively small blending amount thereof makes the paste difficult to handle. Therefore, the blending amount in the paste (ii) is preferably from 20 parts by mass to 70 parts by mass, more preferably from 30 parts by mass to 50 parts by mass with respect to 100 parts by mass of the total amount of (C) the (meth)acrylic acid-based polymerizable monomer in which (A) the (meth)acrylic acid-based polymer has a solubility of 20 mass % or more, and (D) the filler, and in order to obtain a moderate viscosity increase at the time of the mixing of the pastes, the blending amount is preferably from 15 parts by mass to 65 parts by mass with respect to 100 parts by mass of the dental plate liner to be obtained by mixing the paste (i) and the paste (ii).

In addition, in order to suppress an odor and an irritating property, the blending amount of the (meth)acrylic acid-based polymerizable monomers including the component (B) fluorine-containing (meth)acrylic acid-based polymerizable monomer and (C) the (meth)acrylic acid-based polymerizable monomer is preferably 70 parts by mass or less, more preferably 50 parts by mass or less with respect to 100 parts by mass of the dental plate liner to be obtained by mixing the paste (i) and the paste (ii).

In the description of the present application, (D) the filler to be used in the dental plate liner according to this embodiment means a solid material, such as a particulate material, which substantially does not dissolve in all kinds of polymerizable monomers and polymer to be used in the preparation of the paste (i) and the paste (ii), and excludes a solid material compatible with one or more kinds of organic substances selected from the polymerizable monomers and polymer to be used in the preparation of the paste (i) and the paste (ii). For example, as a material which does not correspond to (D) the filler but can take the form of a solid material at least in the paste, there is given (A) a (meth) acrylic acid-based polymer which, when the paste (i) and the paste (ii) are mixed, is compatible with the (meth)acrylic acid-based polymerizable monomers so as to have a smaller particle diameter as compared to that at the time of the preparation of the paste or completely lose its solid form at the time of the preparation of the paste. As (D) the filler satisfying such condition, a known one which may be generally used in a dental material may be used. The filler may be an organic filler, or may be an inorganic filler.

For example, a generally available cross-linked polymer of any one of the following polymers is used as the organic filler without limitation: poly(meth)acrylate, polycarbonate, and polyester. Powder of polymethyl methacrylate, polyethyl methacrylate, polybutyl methacrylate, or polystyrene or a copolymer thereof is typically suitably used from the viewpoints of chemical stability, transparency, and the like. Of those, (meth)acrylic acid-based cross-linked polymer particles of polymethyl methacrylate, polyethyl methacrylate, and the like are particularly suitable because of inexpensiveness and the ease of handling.

The kind of the inorganic filler is not particularly limited, and the inorganic filler may be selected from filling materials added to general dental materials. Specific examples thereof include calcium carbonate, calcium sulfate, magnesium oxide, barium carbonate, barium sulfate, titanium oxide, potassium titanate, barium titanate, aluminum hydroxide, magnesium hydroxide, silica stone powder, glass powder, diatomaceous earth, silica, calcium silicate, talc, alumina, bentonite, zeolite, kaolin clay, mica, and quartz glass. From the viewpoints of, for example, the ease of handling and a dissolution property (elution) into saliva, silica or alumina is suitably used.

The particle diameter of such filler is not particularly limited, but from the viewpoints of paste properties, the filler has an average particle diameter of preferably 100 μm or less, more preferably from 0.01 μm to 40 μm. Two or more kinds of organic or inorganic fillers different from each other in terms of material, average particle diameter, or the like may be used in combination.

The filler may be added without any particular limitation, but from the viewpoints of the mechanical strength of the dental plate liner and paste properties, in the paste (ii), the filler is added in an amount of preferably from 30 parts by mass to 80 parts by mass, more preferably from 50 parts by mass to 70 parts by mass with respect to 100 parts by mass of the total amount of (C) the (meth)acrylic acid-based polymerizable monomer in which (A) the (meth)acrylic acid-based polymer has a solubility of 20 mass % or more and (D) the filler.

As (E) the polymerization initiator to be used in the dental plate liner according to this embodiment, any polymerization initiator capable of allowing (B) the fluorine-containing (meth)acrylic acid-based polymerizable monomer and (C) the (meth)acrylic acid-based polymerizable monomer to be polymerized and cured may be used without any limitation, and a known polymerization initiator may be used. For example, as a radical polymerization initiator to be used in the field of dentistry, there are given a chemical polymerization initiator (normal temperature redox initiator), a photopolymerization initiator, and a thermal polymerization initiator. In consideration of the curing to be performed in the mouth, a chemical polymerization initiator and/or a photopolymerization initiator is preferred.

The chemical polymerization initiator is a polymerization initiator which is formed of two or more components and generates a polymerization active species at around room temperature when all the components are mixed immediately before use. Such chemical polymerization initiator is typically an organic peroxide/amine compound-based one.

Typical examples of the organic peroxide used as such chemical polymerization initiator include a ketone peroxide, a peroxyketal, a hydroperoxide, a diaryl peroxide, a peroxyester, a diacyl peroxide, and a peroxydicarbonate. Specific examples thereof may include methyl ethyl ketone peroxide, cyclohexane peroxide, P-methane hydroperoxide, diisopropylbenzene peroxide, 2,4-dichlorobenzoyl peroxide, lauroyl peroxide, benzoyl peroxide, di-n-propyl peroxydicarbonate, and 1,1,3,3-tetramethylbutyl peroxyneodecanoate.

The suitable usage amount of the organic peroxide varies depending on the kind of the organic peroxide to be used, and hence cannot be limited in a generalized manner, but falls within the range of preferably from 0.05 part by mass to 5 parts by mass, more preferably from 0.1 part by mass to 3 parts by mass with respect to 100 parts by mass of the (meth)acrylic acid-based polymerizable monomers including (B) the fluorine-containing (meth)acrylic acid-based polymerizable monomer and (C) the (meth)acrylic acid-based polymerizable monomer.

In addition, as a tertiary amine for generating a radical through contact with the organic peroxide, a known compound may be used without any particular limitation. Specific examples of the tertiary amine compound, which is suitably used, include: anilines, such as N,N-dimethylaniline, N,N-diethylaniline, N,N-dipropylaniline, N,N-dibutylaniline, and N-methyl-N-β-hydroxyethylaniline; toluidines, such as N,N-dimethyl-p-toluidine, N,N-diethyl-p-toluidine, N,N-dipropyl-p-toluidine, N,N-dibutyl-p-toluidine, p-tolyldiethanolamine, and p-tolyldipropanolamine; anisidines, such as N,N-dimethyl-p-anisidine, N,N-diethyl-p-anisidine, N,N-dipropyl-p-anisidine, and N,N-dibutyl-p-anisidine; morpholines, such as N-phenylmorpholine and N-tolylmorpholine; bis(N,N-dimethylaminophenyl)methane; and bis(N,N-dimethylaminophenyl) ether. Those amine compounds may be used as salts with, for example, hydrochloric acid, phosphoric acid, or an organic acid, such as acetic acid or propionic acid. Of those tertiary amine compounds, N,N-diethyl-p-toluidine, N,N-dipropyl-p-toluidine, p-tolyldiethanolamine, or p-tolyldipropanolamine is suitably used from the viewpoints of high polymerization activity, low stimulation, and low odor.

The usage amount of the tertiary amine compound falls within the range of preferably from 0.05 part by mass to 5 parts by mass, more preferably from 0.1 part by mass to 3 parts by mass with respect to 100 parts by mass of the (meth)acrylic acid-based polymerizable monomers including (B) the fluorine-containing (meth)acrylic acid-based polymerizable monomer and (C) the (meth)acrylic acid-based polymerizable monomer.

Suitable specific examples of the combinations of the organic peroxides and the tertiary amine compounds described above include combinations of: BPO/N,N-diethyl-p-toluidine; BPO/N,N-dipropyl-p-toluidine; BPO/p-tolyldiethanolamine; and BPO/p-tolyldipropanolamine. Of those, when a long period of time of storage is needed under a state in which the tertiary amine compound is mixed with a radically polymerizable monomer, a combination of BPO/N,N-diethyl-p-toluidine or BPO/N,N-dipropyl-p-toluidine is most preferred from the viewpoint of storage stability.

The chemical polymerization initiator formed of the organic peroxide and the amine compound as described above may be used without any problem even when further blended with an initiator based on any of sulfinic acids, such as benzenesulfinic acid and p-toluenesulfinic acid and salts thereof, or barbituric acids, such as 5-butylbarbituric acid.

In addition, any one of the following known initiators is preferably used as the photopolymerization initiator: an α-diketone-reducing agent, a ketal-reducing agent, a thioxanthone-reducing agent, and the like. Examples of the α-diketone may include camphorquinone, benzil, 2,3-pentadione, and 3,4-heptadione. Examples of the ketal may include benzyl dimethyl ketal, benzyl diethyl ketal, and benzyl(2-methoxyethyl ketal). Examples of the thioxanthone may include thioxanthone, 2,4-dimethylthioxanthone, 2,4-diethylthioxanthone, and 2-chlorothioxanthone. As a reducing agent to be used as one component of the photopolymerization initiator, there may be given, for example: tertiary amines, such as 2-(dimethylamino)ethyl methacrylate, ethyl 4-dimethylaminobenzoate, and N-methyldiethanolamine; aldehydes, such as laurylaldehyde, dimethylaminobenzaldehyde, and terephthalaldehyde; 2-mercaptobenzoxazole; 1-decanethiol; thiosalicylic acid; and thiobenzoic acid.

The suitable usage amount of the photopolymerization initiator varies depending on the kind of the photopolymerization initiator to be used, and hence cannot be limited in a generalized manner, but falls within the range of preferably from 0.05 part by mass to 5 parts by mass, more preferably from 0.1 part by mass to 3 parts by mass with respect to 100 parts by mass of the (meth)acrylic acid-based polymerizable monomers including (B) the fluorine-containing (meth)acrylic acid-based polymerizable monomer and (C) the (meth)acrylic acid-based polymerizable monomer.

Herein, when the chemical polymerization initiator containing an organic peroxide and a tertiary amine compound as constituent components is used, any one (E1) of the constituent components is blended into the paste (i), and the other constituent component (E2) is blended into the paste (ii). In addition, when the photopolymerization initiator is used, the photopolymerization initiator may be divided and blended into the paste (i) and the paste (ii), or may be blended into only any one of the pastes. In addition, the chemical polymerization initiator and the photopolymerization initiator may be used in combination.

For example, any one of the following additives may be added to the dental plate liner according to this embodiment: an alcohol or a plasticizer, such as ethanol, dibutyl phthalate, or dioctyl phthalate; a polymerization inhibitor, such as butylhydroxytoluene or methoxyhydroquinone; a UV absorber, such as 4-methoxy-2-hydroxybenzophenone or 2-(2-benzotriazole)-p-cresol; a polymerization modifier, such as an α-methylstyrene dimer; a dye; a pigment; and a perfume. The concentration of any such additive in each of the paste (i) and the paste (ii) is preferably 5 mass % or less, more preferably 3 mass % or less, still more preferably 1 mass % or less.

The paste (i) contains, as main components, (A) the (meth)acrylic acid-based polymer and (B) the fluorine-containing (meth)acrylic acid-based polymerizable monomer. Herein, the content of the main components in the paste (i) falls preferably within the range of from 95 mass % to 100 mass %, more preferably within the range of from 98 mass % to 100 mass %, still more preferably within the range of from 99 mass % to 100 mass %. In addition, the paste (i) may contain a small amount of a polymer other than (A) the (meth)acrylic acid-based polymer, a polymerizable monomer other than (B) the fluorine-containing (meth) acrylic acid-based polymerizable monomer, or a filler, but the content thereof is preferably 3 mass % or less, more preferably 2 mass % or less. However, it is still more preferred that the paste (i) be substantially or completely free of the other polymer, the other polymerizable monomer, and the filler.

In addition, the paste (ii) contains, as main components, (C) the (meth)acrylic acid-based polymerizable monomer and (D) the filler. Herein, the content of the main components in the paste (ii) falls preferably within the range of from 95 mass % to 100 mass %, more preferably within the range of from 98 mass % to 100 mass %, still more preferably within the range of from 99 mass % to 100 mass %. In addition, the paste (ii) may contain a small amount of a polymerizable monomer other than (C) the (meth)acrylic acid-based polymerizable monomer, or a polymer, but the content thereof is preferably 3 mass % or less, more preferably 2 mass % or less. However, it is still more preferred that the paste (ii) be substantially or completely free of the polymer and the other polymerizable monomer.

The paste (i) and the paste (ii) to be used in the dental plate liner according to this embodiment are each a paste-like material. In the description of the present application, the "paste-like material" means a material having a viscosity at 25° C. within the range of from 10 P to 1,000 P. From the viewpoint of workability, the viscosity is preferably from 10 P to 700 P, more preferably from 20 P to 500 P. In addition, the viscosity of the paste (i) is still more preferably from 100 P to 500 P, most preferably from 200 P to 450 P, and the viscosity of the paste (ii) is still more preferably from 20 P to 200 P, most preferably from 30 P to 150 P.

In the dental plate liner according to this embodiment, the mixing ratio between the paste (i) and the paste (ii) is not particularly limited, and may be appropriately determined within a range in which the following three characteristics are obtained: a time-dependent viscosity increase comparable to that of a related-art dental plate liner formed of a powder material and a liquid material can be obtained; coloring of a cured product hardly occurs; and a viscosity change during the storage of the pastes is suppressed. It should be noted that, when there is a large difference between the ratios of the paste (i) and the paste (ii), the paste (i) and the paste (ii) may be difficult to mix homogeneously. Therefore, the mixing ratio between the paste (i) and the paste (ii) on a mass basis is preferably from 10:1 to 1:10, more preferably from 5:1 to 1:5.

In addition, in the case where the dental plate liner according to this embodiment is supplied to product users, such as a dentist and a dental technician, a certain value is specified as the mixing ratio between the paste (i) and the paste (ii) within a range in which the above-mentioned three characteristics are obtained. In this case, a method of specifying the value for the mixing ratio is not particularly limited, and for example, the value for the mixing ratio may be specified by being indicated on: a) a product package formed of a cardboard box or the like; b) an instruction manual for a product to be supplied as a paper medium and/or electronic data; c) a storage member (e.g., a container or a packaging bag) for storing each of the paste (i) and the paste (ii) in a sealed state; d) a product catalog to be supplied as a paper medium and/or electronic data; or e) a written message to be sent to a product user by email, mail matter, or the like separately from a product. In addition, the value for the mixing ratio may also be specified by specifying f) the use of a dedicated measuring cup which, for example, is graduated so as to enable mixing at a predetermined mixing ratio or has a specified weighing capacity, or g) the use of a dedicated mixer configured to enable mixing at a predetermined mixing ratio, in the use of the dental plate liner according to this embodiment.

EXAMPLES

The present invention is specifically described below by way of Examples, but the present invention is not limited to Examples. Evaluating methods for various kinds of physical properties in each of Examples and Comparative Examples are as described below.

(1) Measurement Method for Solubility

To a polymerizable monomer, (A) a (meth)acrylic acid-based polymer was added at a content within the range of from 5 mass % to 50 mass %, and whether or not (A) the (meth)acrylic acid-based polymer dissolved at 23° C. was visually evaluated to measure its solubility. Expressions shown in the column for "solubility" shown later in Table 2 and Table 3 have the following meanings.

(1) The expression "less than 5 mass %": The whole amount of 5 mass % of (A) the (meth)acrylic acid-based polymer does not dissolve in the polymerizable monomer.

(2) The expression "X mass %" (where X represents a value within the range of 5 or more and less than 50): The whole amount of X mass % of (A) the (meth)acrylic acid-based polymer dissolves in the polymerizable monomer.

(3) The expression "50 mass % or more": The whole amount of 50 mass % of (A) the (meth)acrylic acid-based polymer dissolves in the polymerizable monomer.

(2) Measurement Method for Complex Modulus Retention Time

A time-dependent change in complex modulus was measured using a dynamic viscoelasticity measuring apparatus CS Rheometer "CVO120HR" (manufactured by Bohlin) The measurement was performed using a parallel plate having a diameter of 20 mm at a frequency of 1 Hz and a measurement temperature of 37° C. in an oscillation mode. Predetermined amounts of a paste (i) and a paste (ii) were mixed so as to be homogeneous, and the measurement was started 1 minute after the start of the mixing. A period of time required for the complex modulus to change from $10^3$ Pa to $10^4$ Pa, and a period of time required for the complex modulus to change from $10^4$ Pa to $10^6$ Pa were determined and defined as complex modulus retention times.

In clinical use, a state in which a paste to be obtained by mixing a powder material and a liquid material, and a paste to be obtained by mixing two kinds of pastes each have a complex modulus of from about $10^3$ Pa to about $10^4$ Pa is suitable for a stage of being inserted into the mouth and molded, and a state in which the pastes each have a complex modulus of from about $10^4$ Pa to about $10^6$ Pa is suitable for a stage of being removed from the mouth and trimmed. In order to perform each operation with sufficient leeway and to prevent an excessive increase in operation time due to a slow viscosity change, the period of time required for the complex modulus to change from $10^3$ Pa to $10^4$ Pa falls within preferably the range of 30 seconds or more and 2 minutes and 20 seconds or less, more preferably the range of 50 seconds or more and 2 minutes and 00 seconds or less, and the period of time required for the complex modulus to change from $10^4$ Pa to $10^6$ Pa falls within preferably the range of 2 minutes and 00 seconds or more and 6 minutes and 00 seconds or less, more preferably the range of 4 minutes and 00 seconds or more and 5 minutes and 30 seconds or less.

(3) Evaluation of Coloring Resistance

Coloring resistance was evaluated by measuring a coloring amount. For the measurement of the coloring amount, a test piece having a size of 20 mm×20 mm×2 mm was produced. In this case, in each of the experimental examples of Examples 1 to 13 and 16 to 20 and Comparative Examples 1 to 5 using a chemical polymerization initiator, the test piece was produced by pouring a mixture obtained by mixing two kinds of pastes into a mold having upper and lower openings, and curing the mixture under a state in which the mold was sandwiched with transparent plastic sheets from above and below by pressure contact. In addition, in each of the experimental examples of Examples 14 and 15 using a photopolymerization initiator, a member in which a mold having poured thereinto the mixture was sandwiched with transparent plastic sheets from above and below by pressure contact was prepared in the same manner as in each of the experimental examples using a chemical polymerization initiator. Next, the member was placed in a photoirradiation device (manufactured by Tokuyama Corporation, TOKUSO B-L) and irradiated with light for 10 minutes to cure the mixture. Thus, the test piece was produced. The resultant test piece (cured body) was measured for its L*, a*, and b* before coloring with a colorimeter (manufactured by Tokyo Denshoku Co., Ltd., TC-1800MKII). After that, each test piece was immersed in 100 ml of a 20 wt % curry suspension liquid and immersed at 37° C. for 24 hours. After the immersion, the test piece was washed with water and dried, and measured for its L*, a*, and b* again with the colorimeter. The coloring amount (ΔE*) was determined from differences in L*, a*, and b*, i.e., ΔL*, Δa*, and Δb* by using the following equation. In order for coloring to be acceptable in visual observation, ΔE* is preferably about 6.0 or less.

$$\Delta E^* = (\Delta L^{*2} + \Delta a^{*2} + \Delta b^{*2})^{1/2}$$

(4) Evaluation of Storage Stability

Storage stability was evaluated by evaluating paste properties after 1 month. Specifically, the paste (i) and the paste (ii) were each stored at 23° C. under a light shielded condition for 1 month, and the properties of each paste were evaluated. Judging criteria are as follows.
A: A viscosity after 1-month storage shows no change as compared to a viscosity immediately after the preparation of a paste.
B: A slight viscosity change is present immediately after the preparation of a paste.
C: A remarkable viscosity change is present immediately after the preparation of a paste.

In addition, various compounds used in each of Examples and Comparative Examples are as follows.
(A) (Meth)acrylic Acid-Based Polymer
PEMA1: polyethyl methacrylate (average particle diameter: 35 μm, average molecular weight: 400,000)
PEMA2: polyethyl methacrylate (average particle diameter: 70 μm, average molecular weight: 500,000)
PEMA3: polyethyl methacrylate (average particle diameter: 10 μm, average molecular weight: 500,000)
P(EMA-MMA)1: (ethyl methacrylate-methyl methacrylate) copolymer (average particle diameter: 40 μm, average molecular weight: 1,000,000, copolymerization composition ratio (molar ratio): ethyl methacrylate/methyl methacrylate=50/50)
P(EMA-MMA)2: (ethyl methacrylate-methyl methacrylate) copolymer (average particle diameter: 40 μm, average molecular weight: 125,000, copolymerization composition ratio (molar ratio): ethyl methacrylate/methyl methacrylate=40/60)
PMMA: polymethyl methacrylate (average particle diameter: 20 μm, average molecular weight: 250,000)
(B) Fluorine-Containing (Meth)acrylic Acid-Based Polymerizable Monomer in which (A) the (Meth)acrylic Acid-Based Polymer has a Solubility of Less than 20 Mass %
FMA1: 1H,1H,3H-hexafluorobutyl methacrylate
FMA2: perfluorooctylethyl methacrylate
FMA3: perfluorobutylethyl methacrylate
(Meth)acrylic Acid-Based Polymerizable Monomer in which (A) the (Meth)acrylic Acid-Based Polymer has a Solubility of Less than 20 Mass %
PTMG: polytetramethylene glycol dimethacrylate
(C) (Meth)acrylic Acid-Based Polymerizable Monomer in which (A) the (Meth)acrylic Acid-Based Polymer has a Solubility of 20 Mass % or More
ND: 1,9-nonanediol dimethacrylate
HPr: β-methacryloyloxyethyl propionate
HD: 1,6-hexanediol dimethacrylate
Bu-EMA: butoxyethyl methacrylate
(D) Filler
PMMA-X: cross-linked polymethyl methacrylate (average particle diameter: 8 μm)
Silica: fumed silica (monomethyltrichlorosilane treatment, average particle diameter: 0.012 μm)
Silica-zirconia: spherical silica-zirconia filler (3-glycidyloxypropyltrimethoxysilane treatment, average particle diameter: 0.4 μm)
(E) Polymerization Initiator
BPO: benzoyl peroxide
CQ: camphorquinone
DEPT: N,N-diethyl-p-toluidine
DMPT: N,N-dimethyl-p-toluidine Example 1

The paste (i) and the paste (ii) were each produced with composition shown in Table 1. The pastes were mixed with equal weight, and each of the physical properties was evaluated. The following items are shown in Table 2: evaluation result of each of the physical properties and the solubility of (A) the (meth)acrylic acid-based polymer in each polymerizable monomer, i.e., each of (B) the fluorine-containing (meth)acrylic acid-based polymerizable monomer and (C) the (meth)acrylic acid-based polymerizable monomer.

TABLE 1

| | Paste (i) | | | | | | | Paste (ii) | |
| | (A) (Meth)acrylic acid-based polymer | | (B) Fluorine-containing (meth)acrylic acid-based polymerizable monomer | | (E1) Polymerization initiator | | | (C) (Meth)acrylic acid-based polymerizable monomer | |
| | Kind | Blending amount (parts by mass) | Kind | Blending amount (parts by mass) | Kind | Blending amount (parts by mass) | Paste viscosity (P) | Kind | Blending amount (parts by mass) |
|---|---|---|---|---|---|---|---|---|---|
| Example 1 | PEMA1 | 60 | FMA1 | 40 | BPO | 1 | 344 | ND | 40 |
| Example 2 | PEMA1 | 60 | FMA2 | 40 | BPO | 1 | 364 | ND | 40 |

TABLE 1-continued

| | | | | | | | | |
|---|---|---|---|---|---|---|---|---|
| Example 3 | PEMA1 | 60 | FMA3 | 40 | BPO | 1 | 308 | ND | 40 |
| Example 4 | PEMA2 | 60 | FMA1 | 40 | BPO | 1 | 290 | ND | 40 |
| Example 5 | PEMA3 | 60 | FMA1 | 40 | BPO | 1 | 392 | ND | 40 |
| Example 6 | P(EMA-MMA)1 | 60 | FMA1 | 40 | BPO | 1 | 271 | ND | 40 |
| Example 7 | P(EMA-MMA)2 | 60 | FMA1 | 40 | BPO | 1 | 360 | ND | 40 |
| Example 8 | PMMA | 60 | FMA1 | 40 | BPO | 1 | 283 | ND | 40 |
| Example 9 | PEMA1 | 60 | FMA1 | 40 | BPO | 1 | 341 | HPr | 40 |
| Example 10 | PEMA1 | 60 | FMA1 | 40 | BPO | 1 | 344 | ND/HPr | 20/20 |
| Example 11 | PEMA1 | 60 | FMA1 | 40 | BPO | 1 | 347 | ND | 40 |
| Example 12 | PEMA1 | 60 | FMA1 | 40 | BPO | 1 | 340 | ND | 40 |
| Example 13 | PEMA1 | 60 | FMA1 | 40 | DEPT | 1 | 345 | ND | 40 |
| Example 14 | PEMA1 | 60 | FMA1 | 40 | CQ/DMPT | 0.4/1.1 | 349 | ND | 40 |
| Example 15 | PEMA1 | 60 | FMA1 | 40 | — | — | 344 | ND | 40 |
| Example 16 | PEMA1 | 48 | FMA1 | 52 | BPO | 1 | 285 | ND | 40 |
| Example 17 | PEMA1 | 60 | FMA1 | 40 | BPO | 1 | 342 | ND | 50 |
| Example 18 | PEMA1 | 30 | FMA1 | 70 | BPO | 1 | 240 | ND | 30 |
| Example 19 | PEMA1 | 75 | FMA1 | 25 | BPO | 1 | 411 | ND | 75 |
| Example 20 | PEMA1 | 60 | FMA1 | 40 | BPO | 1 | 342 | ND | 75 |
| Example 21 | PEMA1 | 75 | FMA1 | 25 | BPO | 1 | 410 | ND | 40 |

| | Paste (ii) | | | | | | |
|---|---|---|---|---|---|---|---|
| | (D) Filler | | (E2) Polymerization initiator | | | | Paste mixing ratio (i)/(ii) |
| | Kind | Blending amount (parts by mass) | Kind | Blending amount (parts by mass) | Paste viscosity (P) | Blending ratio (A)/(C) | |
| Example 1 | PMMA-X | 60 | DEPT | 1 | 74 | 1.5 | 1/1 |
| Example 2 | PMMA-X | 60 | DEPT | 1 | 76 | 1.5 | 1/1 |
| Example 3 | PMMA-X | 60 | DEPT | 1 | 70 | 1.5 | 1/1 |
| Example 4 | PMMA-X | 60 | DEPT | 1 | 71 | 1.5 | 1/1 |
| Example 5 | PMMA-X | 60 | DEPT | 1 | 69 | 1.5 | 1/1 |
| Example 6 | PMMA-X | 60 | DEPT | 1 | 75 | 1.5 | 1/1 |
| Example 7 | PMMA-X | 60 | DEPT | 1 | 72 | 1.5 | 1/1 |
| Example 8 | PMMA-X | 60 | DEPT | 1 | 70 | 1.5 | 1/1 |
| Example 9 | PMMA-X | 60 | DEPT | 1 | 90 | 1.5 | 1/1 |
| Example 10 | PMMA-X | 60 | DEPT | 1 | 81 | 1.5 | 1/1 |
| Example 11 | Silica | 60 | DEPT | 1 | 141 | 1.5 | 1/1 |
| Example 12 | Silica-zirconia | 60 | DEPT | 1 | 118 | 1.5 | 1/1 |
| Example 13 | PMMA-X | 60 | BPO | 1 | 75 | 1.5 | 1/1 |
| Example 14 | PMMA-X | 60 | — | — | 73 | 1.5 | 1/1 |
| Example 15 | PMMA-X | 60 | CQ/DMPT | 0.4/1.1 | 73 | 1.5 | 1/1 |
| Example 16 | PMMA-X | 60 | DEPT | 1 | 71 | 1.2 | 1/1 |
| Example 17 | PMMA-X | 50 | DEPT | 1 | 57 | 1.2 | 1/1 |
| Example 18 | PMMA-X | 70 | DEPT | 1 | 99 | 1.0 | 1/1 |
| Example 19 | PMMA-X | 25 | DEPT | 1 | 34 | 1.0 | 1/1 |
| Example 20 | PMMA-X | 25 | DEPT | 1 | 33 | 0.19 | 1/4 |
| Example 21 | PMMA-X | 60 | DEPT | 1 | 74 | 2.8 | 3/2 |

TABLE 2

| | Solubility of (A) (meth)acrylic acid-based polymer | | | | Coloring amount ΔE* | Paste properties after 1 month | |
|---|---|---|---|---|---|---|---|
| | (B) Fluorine-containing (meth)acrylic acid-based polymerizable monomer | (C) (Meth)acrylic acid-based polymerizable monomer | Complex modulus retention time | | | Paste (i) | Paste (ii) |
| | | | From $10^3$ Pa to $10^4$ Pa | From $10^4$ Pa to $10^6$ Pa | | | |
| Example 1 | Less than 5 mass % | 50 mass % or more | 1 minute and 05 seconds | 4 minutes and 53 seconds | 5.1 | A | A |
| Example 2 | Less than 5 mass % | 50 mass % or more | 1 minute and 00 seconds | 5 minutes and 02 seconds | 5.3 | A | A |
| Example 3 | Less than 5 mass % | 50 mass % or more | 1 minute and 08 seconds | 4 minutes and 45 seconds | 5.2 | A | A |
| Example 4 | Less than 5 mass % | 50 mass % or more | 1 minute and 09 seconds | 5 minutes and 15 seconds | 5.3 | A | A |
| Example 5 | 17 mass % | 50 mass % or more | 55 seconds | 3 minutes and 57 seconds | 5.0 | B | A |

TABLE 2-continued

Solubility of (A) (meth)acrylic acid-based polymer

| | (B) Fluorine-containing (meth)acrylic acid-based polymerizable monomer | (C) (Meth)acrylic acid-based polymerizable monomer | Complex modulus retention time | | Coloring amount | Paste properties after 1 month | |
|---|---|---|---|---|---|---|---|
| | | | From $10^3$ Pa to $10^4$ Pa | From $10^4$ Pa to $10^6$ Pa | $\Delta E^*$ | Paste (i) | Paste (ii) |
| Example 6 | Less than 5 mass % | 31 mass % | 1 minute and 18 seconds | 4 minutes and 48 seconds | 4.9 | B | A |
| Example 7 | Less than 5 mass % | 24 mass % | 1 minute and 00 seconds | 4 minutes and 59 seconds | 5.6 | B | A |
| Example 8 | Less than 5 mass % | 34 mass % | 1 minute and 16 seconds | 5 minutes and 23 seconds | 4.9 | B | A |
| Example 9 | Less than 5 mass % | 50 mass % or more | 51 seconds | 4 minutes and 01 seconds | 5.0 | A | A |
| Example 10 | Less than 5 mass % | 50 mass % or more | 58 seconds | 4 minutes and 32 seconds | 5.1 | A | A |
| Example 11 | Less than 5 mass % | 50 mass % or more | 1 minute and 05 seconds | 5 minutes and 01 seconds | 4.8 | A | A |
| Example 12 | Less than 5 mass % | 50 mass % or more | 1 minute and 06 seconds | 4 minutes and 58 seconds | 4.7 | A | A |
| Example 13 | Less than 5 mass % | 50 mass % or more | 1 minute and 06 seconds | 4 minutes and 52 seconds | 5.0 | A | A |
| Example 14 | Less than 5 mass % | 50 mass % or more | 1 minute and 03 seconds | 5 minutes and 10 seconds | 5.0 | A | A |
| Example 15 | Less than 5 mass % | 50 mass % or more | 1 minute and 08 seconds | 5 minutes and 12 seconds | 5.2 | A | A |
| Example 16 | Less than 5 mass % | 50 mass % or more | 1 minute and 13 seconds | 4 minutes and 40 seconds | 4.7 | A | A |
| Example 17 | Less than 5 mass % | 50 mass % or more | 1 minute and 03 seconds | 4 minutes and 48 seconds | 5.1 | A | A |
| Example 18 | Less than 5 mass % | 50 mass % or more | 55 seconds | 4 minutes and 59 seconds | 4.6 | A | A |
| Example 19 | Less than 5 mass % | 50 mass % or more | 1 minute and 14 seconds | 4 minutes and 27 seconds | 5.5 | A | A |
| Example 20 | Less than 5 mass % | 50 mass % or more | 2 minutes and 08 seconds | 5 minutes and 09 seconds | 7.9 | A | A |
| Example 21 | Less than 5 mass % | 50 mass % or more | 35 seconds | 5 minutes and 08 seconds | 7.6 | A | A |

As shown in Table 2, the period of time required for the complex modulus to change from $10^3$ Pa to $10^4$ Pa, and the period of time required for the complex modulus to change from $10^4$ Pa to $10^6$ Pa were sufficiently kept, and a moderate viscosity increase comparable to that of a related-art dental plate liner including a powder material and a liquid material (Reference Example to be described later) was observed. $\Delta E^*$ in the curry coloring test was 5.1, indicating excellent coloring resistance, and the paste properties after 1 month did not show a change from immediately after paste production, indicating satisfactory storage stability. Needless to say, the operation of mixing a powder material and a liquid material was not performed, the mixing operation was extremely easy, and workability was also extremely excellent.

Examples 2 and 3

Evaluations were performed in the same manner as in Example 1 except that the kind of (B) the fluorine-containing (meth)acrylic acid-based polymerizable monomer in which (A) the (meth)acrylic acid-based polymer had a solubility of less than 20 mass % was changed as shown in Table 1. The evaluation results of the various physical properties, and the solubility of (A) the (meth)acrylic acid-based polymer in each polymerizable monomer, i.e., each of (B) the fluorine-containing (meth)acrylic acid-based polymerizable monomer and (C) the (meth)acrylic acid-based polymerizable monomer are shown in Table 2.

As shown in Table 2, each example was observed to have a moderate viscosity increase, and was found to be excellent in coloring resistance and storage stability.

Examples 4 to 8

Evaluations were performed in the same manner as in Example 1 except that the kind of (A) the (meth)acrylic acid-based polymer was changed as shown in Table 1. The evaluation results of the various physical properties, and the solubility of (A) the (meth)acrylic acid-based polymer in each polymerizable monomer, i.e., each of (B) the fluorine-containing (meth)acrylic acid-based polymerizable monomer and (C) the (meth)acrylic acid-based polymerizable monomer are shown in Table 2.

As (A) the (meth)acrylic acid-based polymer had a larger particle diameter and a larger molecular weight, the complex modulus retention times tended to become longer and the viscosity increase tended to be slowed. However, each example provided a moderate viscosity increase, and was extremely excellent in coloring resistance, storage stability, and workability.

Examples 9 and 10

Evaluations were performed in the same manner as in Example 1 except that the kind of (C) the (meth)acrylic acid-based polymerizable monomer in which (A) the (meth)acrylic acid-based polymer had a solubility of 20 mass % or more was changed as shown in Table 1. The solubility of (A) the (meth)acrylic acid-based polymer in each polymerizable monomer, i.e., each of (B) the fluorine-containing (meth)acrylic acid-based polymerizable monomer and (C) the (meth)acrylic acid-based polymerizable monomer is shown in Table 2.

As shown in Table 2, it was found that each example provided a moderate viscosity increase, and was extremely excellent in coloring resistance, storage stability, and workability.

Examples 11 and 12

Evaluations were performed in the same manner as in Example 1 except that the kind of (D) the filler was changed as shown in Table 1. The solubility of (A) the (meth)acrylic acid-based polymer in each polymerizable monomer, i.e., each of (B) the fluorine-containing (meth)acrylic acid-based polymerizable monomer and (C) the (meth)acrylic acid-based polymerizable monomer is shown in Table 2.

As shown in Table 2, it was found that, even when the inorganic filler was used, as in Example 1, a moderate viscosity increase was obtained, and coloring resistance, storage stability, and workability were extremely excellent.

Example 13

Evaluations were performed in the same manner as in Example 1 except that the kind of (E) the polymerization initiator was changed as shown in Table 1. The solubility of (A) the (meth)acrylic acid-based polymer in each polymerizable monomer, i.e., each of (B) the fluorine-containing (meth)acrylic acid-based polymerizable monomer and (C) the (meth)acrylic acid-based polymerizable monomer is shown in Table 2.

As shown in Table 2, it was found that, irrespective of whether the organic peroxide and the tertiary amine compound were blended into the paste (i) and the paste (ii), respectively, or vice versa, each example provided a moderate viscosity increase, and was extremely excellent in coloring resistance, storage stability, and workability.

Examples 14 and 15

Evaluations were performed in the same manner as in Example 1 except that the kind and the blending amount of (E) the polymerization initiator were changed as shown in Table 1. The evaluation results of the various physical properties, and the solubility of (A) the (meth)acrylic acid-based polymer in each polymerizable monomer, i.e., each of (B) the fluorine-containing (meth)acrylic acid-based polymerizable monomer and (C) the (meth)acrylic acid-based polymerizable monomer are shown in Table 2.

As shown in Table 2, it was found that, even when the photopolymerization initiator was used, each example provided a moderate viscosity increase, and was extremely excellent in coloring resistance, storage stability, and workability.

Examples 16 to 19

Evaluations were performed in the same manner as in Example 1 except that the blending ratio (A)/(C) was changed. The evaluation results of the various physical properties, and the solubility of (A) the (meth)acrylic acid-based polymer in each polymerizable monomer, i.e., each of (B) the fluorine-containing (meth)acrylic acid-based polymerizable monomer and (C) the (meth)acrylic acid-based polymerizable monomer are shown in Table 2.

As shown in Table 2, each example was observed to have a moderate viscosity increase, and was found to be excellent in coloring resistance and storage stability.

Example 20

The paste (i) and the paste (ii) were each produced with composition shown in Table 1. The paste (i) and the paste (ii) were mixed at a weight ratio of 1/4, and the various physical properties were evaluated. The evaluation results of the various physical properties, and the solubility of (A) the (meth)acrylic acid-based polymer in each polymerizable monomer, i.e., each of (B) the fluorine-containing (meth)acrylic acid-based polymerizable monomer and (C) the (meth)acrylic acid-based polymerizable monomer are shown in Table 2.

As shown in Table 2, each example was observed to have a moderate viscosity increase, and was found to be excellent in coloring resistance and storage stability.

Example 21

The paste (i) and the paste (ii) were each produced with composition shown in Table 1. The paste (i) and the paste (ii) were mixed at a weight ratio of 3/2, and the various physical properties were evaluated. The evaluation results of the various physical properties, and the solubility of (A) the (meth)acrylic acid-based polymer in each polymerizable monomer, i.e., each of (B) the fluorine-containing (meth)acrylic acid-based polymerizable monomer and (C) the (meth)acrylic acid-based polymerizable monomer are shown in Table 2.

As shown in Table 2, each example was observed to have a moderate viscosity increase, and was found to be excellent in coloring resistance and storage stability.

REFERENCE EXAMPLE

For reference, "Tokuyama Rebase II" (manufactured by Tokuyama Dental Corporation), which was a dental plate liner to be used through mixing of a powder material and a liquid material, was evaluated by mixing the powder material and the liquid material in accordance with the instruction manual. The results are shown in Table 3.

TABLE 3

| | Solubility of component corresponding to (A) (meth)acrylic acid-based polymer | | | | | Paste properties after 1 month | |
|---|---|---|---|---|---|---|---|
| | Polymerizable monomer in paste (i) | Polymerizable monomer in paste (ii) | Complex modulus retention time | | Coloring amount ΔE* | Paste (i) | Paste (ii) |
| | | | From $10^3$ Pa to $10^4$ Pa | From $10^4$ Pa to $10^6$ Pa | | | |
| Reference Example | — | — | 53 seconds | 4 minutes and 21 seconds | 8.5 | — | — |
| Comparative Example 1 | 50 mass % or more | 50 mass % or more | — | — | — | C | A |
| Comparative Example 2 | — | — | 7 seconds | 26 seconds | 11.2 | A | A |
| Comparative Example 3 | Less than 5 mass % | Less than 5 mass % | 5 seconds | 28 seconds | 4.1 | A | A |
| Comparative Example 4 | 50 mass % or more | 50 mass % or more | 5 minutes and 54 seconds | 23 seconds | 9.3 | C | C |
| Comparative Example 5 | Less than 5 mass % | 50 mass % or more | 2 minutes and 25 seconds | 1 minute and 30 seconds | 10.1 | A | C | erizable monomer and (C) the (meth)acrylic acid-based polymerizable monomer are shown in Table 2.

As shown in Table 3, "Tokuyama Rebase II" was found to have sufficient complex modulus retention times.

Comparative Example 1

The paste (i) having composition in which (B) the fluorine-containing (meth)acrylic acid-based polymerizable monomer of Example 1 was replaced with (C) the (meth) acrylic acid-based polymerizable monomer as shown in Table 4 was produced.

TABLE 4

| | Paste (i) | | | | | | | Paste (ii) | |
|---|---|---|---|---|---|---|---|---|---|
| | Polymer or filler | | Polymerizable monomer | | Polymerization initiator | | | Polymer or filler | |
| | Kind | Blending amount (parts by mass) | Kind | Blending amount (parts by mass) | Kind | Blending amount (parts by mass) | Paste viscosity (P) | Kind | Blending amount (parts by mass) |
| Reference Example | Tokuyama Rebase II (manufactured by Tokuyama Dental Corporation) | | | | | | | | |
| Comparative Example 1 | PEMA1 | 60 | ND | 40 | BPO | 1 | 344 | PMMA-X | 60 |
| Comparative Example 2 | PMMA-X | 60 | ND | 40 | BPO | 1 | 72 | PMMA-X | 60 |
| Comparative Example 3 | PMMA-X | 65 | FMA1 | 35 | BPO | 1 | 108 | PMMA-X | 65 |
| Comparative Example 4 | PEMA1 | 10 | ND | 90 | BPO | 1 | 122 | PEMA1 | 10 |
| Comparative Example 5 | P(EMA-MMA)2 | 30 | PTMG | 70 | DEPT | 1 | 189 | P(EMA-MMA)2 | 20 |

| | Paste (ii) | | | | | | |
|---|---|---|---|---|---|---|---|
| | Polymerizable monomer | | Polymerization initiator | | | Blending ratio Polymer/ Polymerizable monomer | Paste mixing ratio (i)/(ii) |
| | Kind | Blending amount (parts by mass) | Kind | Blending amount (parts by mass) | Paste viscosity (P) | | |
| Reference Example | Tokuyama Rebase II (manufactured by Tokuyama Dental Corporation) | | | | | 1.7 | |
| Comparative Example 1 | ND | 40 | DEPT | 1 | 74 | 0.75 | 1/1 |
| Comparative Example 2 | ND | 40 | DEPT | 1 | 73 | 0 | 1/1 |
| Comparative Example 3 | FMA1 | 35 | DEPT | 1 | 106 | 0 | 1/1 |
| Comparative Example 4 | ND | 90 | DEPT | 1 | 117 | 0.11 | 1/1 |
| Comparative Example 5 | HD/Bu-EMA | 60/20 | BPO | 1 | 150 | 0.63 | 1/1 |

However, because the paste (i) contained the polymerizable monomer in which the (meth)acrylic acid-based polymer had a solubility of 20 mass % or more, PEMA1 dissolved in ND to increase viscosity, resulting in a dough state at the time of the production of the paste (i). Accordingly, the operation of mixing the paste (i) and the paste (ii) was difficult, and physical properties were not able to be evaluated except for paste properties after 1 month.

Comparative Example 2

The paste (i) and the paste (ii) were each produced with composition shown in Table 4 and evaluated in the same manner as in Example 1. The results are shown in Table 3.

Each of the paste (i) and the paste (ii) was prepared as a paste containing, as main components, PMMA-X serving as a filling material and ND serving as a (meth)acrylic acid-based polymerizable monomer. Accordingly, there was no polymer to dissolve when the pastes were mixed, and hence the mixture instantly cured after keeping a constant complex modulus of less than $10^3$ Pa, and a moderate viscosity increase was not obtained. In addition, it was found that the mixture was poor in coloring resistance.

Comparative Example 3

The paste (i) and the paste (ii) were each produced with composition shown in Table 4 and evaluated in the same manner as in Example 1. The results are shown in Table 3.

Each of the paste (i) and the paste (ii) of Comparative Example 3 contains PMMA-X serving as a filler and (B) the fluorine-containing (meth)acrylic acid-based polymerizable monomer (FMA1). Even when the paste (i) and the paste (ii) were mixed, in the mixture, there was no polymer capable of dissolving in the fluorine-containing (meth)acrylic acid-based polymerizable monomer. Accordingly, the mixture instantly cured after keeping a constant complex modulus of less than $10^3$ Pa, and a moderate viscosity increase was not obtained.

Comparative Example 4

The paste (i) and the paste (ii) were each produced with composition shown in Table 4 and evaluated in the same manner as in Example 1. The results are shown in Table 3.

The paste (i) contained the monomer in which the (meth)acrylic acid-based polymer had a solubility of 20 mass % or more, and hence the (meth)acrylic acid-based polymer dissolved in the monomer at the time of the preparation of the paste (i). In addition, the paste (ii) contained the (meth)acrylic acid-based polymer, and hence the (meth)acrylic acid-based polymer dissolved in the monomer in which the (meth)acrylic acid-based polymer had a solubility of 20 mass % or more at the time of the preparation of the paste (ii). Accordingly, even when the paste (i) and the paste (ii) were mixed, the amount of the polymer to dissolve was small, and the mixture instantly cured after keeping a constant complex modulus between $10^3$ Pa and $10^4$ Pa instead of gradually increasing viscosity. Therefore, a moderate viscosity increase was not obtained. In addition, within 1 month after the preparation of the pastes, the polymer remaining owing to its incapability to completely dissolve in a short period of time gradually dissolved during storage to cause a paste viscosity change, and thus storage stability was also found to be poor.

Comparative Example 5

The paste (i) and the paste (ii) were each produced with composition shown in Table 4 and evaluated in the same manner as in Example 1. The results are shown in Table 3. This Comparative Example is a reproduction of Example 1 disclosed in Patent Literature 5.

The paste (ii) contained the (meth)acrylic acid-based polymer, and hence the (meth)acrylic acid-based polymer dissolved in the polymerizable monomer in which the (meth)acrylic acid-based polymer had a solubility of 20 mass % or more. Accordingly, the viscosity increase effect was small, and the state of from $10^4$ Pa to $10^6$ Pa suitable for the trimming stage was for 2 minutes or less, which was insufficient. Thus, workability was found to be poor. In addition, it was found that, because the fluorine-containing (meth)acrylic acid-based polymerizable monomer was not blended, coloring resistance was poor.

The invention claimed is:

1. A dental plate liner, comprising:
   a paste (i) consisting essentially of:
   (A) a non-cross-linked (meth)acrylic acid-based polymer, and
   (B) a fluorine-containing (meth)acrylic acid-based polymerizable monomer in which (A) the (meth)acrylic acid-based polymer has a solubility of less than 20 mass %; and
   a paste (ii) consisting essentially of:
   (C) a (meth)acrylic acid-based polymerizable monomer, which does not contain fluorine and in which (A) the non-cross-linked (meth)acrylic acid-based polymer has a solubility of 20 mass % or more, and
   (D) a filler, which is selected from the group consisting of a cross-linked polymer and an inorganic filler,
   wherein the paste (ii) does not contain (A) the non-cross-linked (meth)acrylic acid-based polymer,
   wherein at least one paste selected from the group consisting of the paste (i) and the paste (ii) contains (E) a polymerization initiator, and
   wherein the dental plate liner is used through mixing of the paste (i) and the paste (ii) immediately before use.

2. A dental plate liner according to claim 1, wherein the dental plate liner consists of the paste (i) and the paste (ii).

3. A dental plate liner according to claim 1, wherein (B) the fluorine-containing (meth)acrylic acid-based polymerizable monomer in which (A) the (meth)acrylic acid-based polymer has a solubility of less than 20 mass % is represented by the following formula (I):

$$CH_2=CR^1COOR^2-Rf \qquad (I)$$

in the formula (I), $R^1$ represents a hydrogen atom or a methyl group, $R^2$ represents an alkyl group having 1 to 20 carbon atoms, and Rf represents a fluoroalkyl group having 1 to 20 carbon atoms.

4. A dental plate liner according to claim 1, wherein (D) the filler comprises (meth)acrylic acid-based cross-linked polymer particles.

5. A dental plate liner according to claim 1, wherein the blending ratio ((A)/(C)) of (A) the (meth)acrylic acid-based polymer to (C) the (meth)acrylic acid-based polymerizable monomer in which (A) the (meth)acrylic acid based polymer has a solubility of 20 mass % or more is from 0.9 to 2.5.

6. A dental plate liner according to claim 1, wherein the blending ratio ((A)/(C)) of (A) the (meth)acrylic acid-based polymer to (C) the (meth)acrylic acid-based polymerizable monomer in which (A) the (meth)acrylic acid based polymer has a solubility of 20 mass % or more is from 0.9 to 3.0.

7. A dental plate liner according to claim 1, wherein the (B) (meth)acrylic acid-based polymerizable monomer is one in which (A) the (meth)acrylic acid-based polymer has a solubility of less than 5 mass % and the (C) (meth)acrylic acid-based polymerizable monomer is one in which (A) the (meth)acrylic acid-based polymer has a solubility of 50 mass % or more.

* * * * *